United States Patent [19]
Mathews

[11] Patent Number: 5,431,170
[45] Date of Patent: Jul. 11, 1995

[54] PULSE RESPONSIVE DEVICE

[76] Inventor: Geoffrey R. Mathews, New House Farm, Llangwm, USK, Gwent, United Kingdom, NP5 1HJ

[21] Appl. No.: 938,179
[22] PCT Filed: May 28, 1991
[86] PCT No.: PCT/GB91/00841
§ 371 Date: Nov. 25, 1992
§ 102(e) Date: Nov. 25, 1992
[87] PCT Pub. No.: WO91/18550
PCT Pub. Date: Dec. 12, 1991

[30] Foreign Application Priority Data
May 26, 1990 [GB] United Kingdom ............... 9011887

[51] Int. Cl.⁶ ............................................ A61B 5/00
[52] U.S. Cl. ................... 128/666; 128/633; 128/687
[58] Field of Search .......... 128/633, 664, 665, 687, 128/688, 689, 903, 690, 782, 666, 715, 667

[56] References Cited
U.S. PATENT DOCUMENTS

| | | | |
|---|---|---|---|
| 4,063,551 | 12/1977 | Sweeney | 128/666 |
| 4,100,536 | 7/1978 | Ball et al. | 128/689 X |
| 4,338,950 | 7/1982 | Barlow, Jr. et al. | 128/782 X |
| 4,409,983 | 10/1983 | Albert | 128/690 |
| 4,566,461 | 1/1986 | Labell et al. | 128/668 |
| 4,723,555 | 9/1988 | Shue | 128/715 |
| 4,819,860 | 4/1989 | Hargrove et al. | 128/668 |
| 4,911,167 | 3/1990 | Corenman et al. | 128/633 |
| 5,003,984 | 4/1991 | Muraki et al. | 128/710 |

FOREIGN PATENT DOCUMENTS
2634050 2/1978 Germany.

Primary Examiner—Angela D. Sykes
Attorney, Agent, or Firm—Edwin D. Schindler

[57] ABSTRACT

A pulse responsive device, for example, a pulse rate meter or pulse oximetry device, is disclosed, which includes a light emitter and a light sensor for receiving light from the emitter after transmission through, or reflection from, body tissue to give an electrical signal varying according to blood flow or other fluid pulsations. A movement transducer gives an additional electrical signal representing body movements or vibrations, but independent of blood flow pulsations. This movement transducer may include a light emitter and sensor responsive to a different wavelength from the light emitter and light sensor used for measuring, and varying with, blood flow or other fluid pulsations. The pulse responsive device compares the two electrical signals produced to cancel out the movement or vibration noise fro the signal obtained from the light sensor which obtains measurements which vary with blood or other fluid flow pulsations.

13 Claims, 2 Drawing Sheets

PULSE RESPONSIVE DEVICE

BACKGROUND OF THE INVENTION

1. Technical Field of the Invention

This invention relates to pulse responsive devices and more particularly but not solely to pulse rate meters and pulse oximetry devices.

2. Description of the Prior Art

Pulse oximetry devices, and some other pulse responsive devices, utilise the effect that there is a change in the light transmitted through or reflected from body tissues, due to the pulsing of the blood flow or flow of other body fluid. Such pulse responsive devices include light sensors which produce electrical output signals which can be analyzed to determine various parameters such as pulse rate or blood oxygen saturation for example. Advantages of these devices are that they are non-invasive and they can monitor the relevant parameter on a continuous basis. However, we have found that movements of the body can generate spurious noise in the output signal of the light sensor, thus masking the signal which is to be monitored. We have now devised a device which overcomes this problem.

SUMMARY OF THE INVENTION

In accordance with this invention, there is provided a pulse responsive device, having a light emitter, a light sensor for receiving light from the emitter after transmission through or reflection from body tissue and providing an electrical signal having a component varying according to pulsations in blood or other fluid flow through the body tissue, and a transducer responsive to movement or vibration of the body and providing an electrical signal varying according to the body movements or vibrations but independent or relatively independent of the blood or other fluid flow pulsations, and means for comparing one electrical signal with the other.

The electrical signal provided by the light sensor includes, in addition to the component varying according to the pulsations in the blood flow, a noise component due to the body movements or vibrations. Accordingly, by comparing one electrical signal with the other, the noise component due to body movements can be cancelled and an output signal is produced which various with the blood pulsations and independently of the body movements.

The movement transducer may comprise a light sensor responsive to light transmitted through or reflected from the body tissue, this light being of a wavelength that is unaffected or substantially unaffected by the pulsations in the flow of blood or other body fluids. As an example, we have found that yellow light is suitable for this purpose. However, as an alternative, the movement transducer may comprise a pressure or vibration sensor or an accelerometer. The two electrical signals may be compared by subtracting one from the other to cancel the noise component. Alternatively, the signal from the movement transducer may be analyzed to identify one or more ranges of frequencies corresponding to noise, and the corresponding frequencies are filtered out from the signal from the light sensor. The frequency analysis of each signal may be carried out by fast Fourier Transform techniques.

An adaptive cancellation technique may be used for subtracting the one electrical signal from the other in which cross-correlation is performed between the two electrical signals, and the technique is therefore able to cancel the noise component even if the phase and amplitude relations of the two signals vary with time.

The pulse responsive device in accordance with this invention may comprise a pulse rate meter. This may be adapted for use by joggers. Preferably in this case the light sensor and movement transducer are applied to the forehead. Preferably a read-out device is provided for wearing on the wrist or the back of the hand. Preferably a short wave radio system communicates output signals from the elements on the forehead to the read-out device on the wrist or hand, but instead the read-out unit may be connected to the elements on the forehead by a cable: the read-out unit may be carried in a pocket or clipped onto the user's clothing. In a modification, the read-out device may also be mounted to the head and provide a visual display coupled to the wearer's spectacles. Instead, the entire pulse responsive device may be arranged for wearing on the wrist or the back of the hand.

Also in accordance with this invention, there is provided a pulse rate meter comprising a sensor unit for wearing against the forehead of a user, a read-out device, and a short-wave radio communication system for transmitting an output signal or output signals from the sensor unit to the read-out device.

Further in accordance with this invention, there is provided a pulse rate meter which keeps cumulative measure of the time that the measured pulse rate has exceeded a predetermined threshold. Preferably this threshold is the lower limit of a training zone, i.e. a range of values between which the user should maintain his or her pulse rate when training. The predetermined threshold may be entered directly into the meter by the user, or may be calculated by the meter from personal data entered by the user, e.g. sex, age, resting pulse rate.

Yet further in accordance with this invention, there is provided a pulse rate meter which has an analogue indicator for displaying measured pulse rate. which is recalibrated upon entering predetermined data. Preferably the analogue indicator includes a "window" corresponding to a training zone and is recalibrated upon entering data which determines this training zone: either the limits of the training zone can be entered directly, or they can be calculated by the meter from personal data entered by the user, e.g. sex, age, resting pulse rate. The resting pulse rate may be measured by the meter when the user is at rest. The lower end of the analogue indicator, upon recalibration, preferably corresponds to the resting pulse rate.

The pulse responsive device may be in the form of a pulse oximetry device. In such case, and in accordance with known principles, two light emitters and two light sensors are provided, operating at two different wavelengths typically 940 nm (infrared) and 660 nm (red). The peak-to-peak amplitude variation in each sensor output signal is determined: the ration between the two peak-to-peak amplitudes gives a measure of the blood oxygen saturation level. However, in accordance with this invention, a movement transducer is also provided (of any of the types described above) to give a signal varying with body movements or vibrations but substantially independent of blood pulsations: this signal is compared with the signals from the two light sensors to cancel the body movement or "noise" components from them, before their peak-to-peak amplitudes are measured and the ratio between those amplitudes is formed.

BRIEF DESCRIPTION OF THE DRAWING FIGURES

An embodiment of this invention will not be described by way of example only and with reference to the accompanying drawings, in which.

DETAILED DESCRIPTION OF THE DRAWING FIGURES

Figure 1:
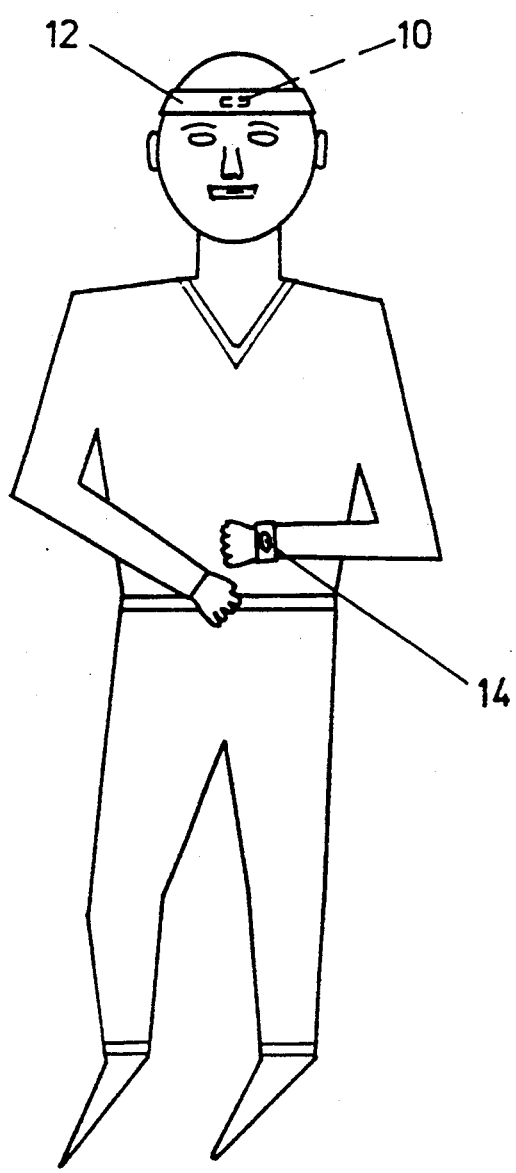
FIG. 1 is a view of a jogger wearing a pulse rate meter in accordance with this invention.

Referring to FIG. 1, there is shown a jogger wearing a pulse rate meter in accordance with this invention.

The example of pulse rate meter which is shown comprises a sensor unit 10 attached to a headband 12 so that the sensor unit is applied against the forehead when the headband is being worn. The meter also comprises a read-out device 14 which in the example shown may have a strap for attaching it around the wrist, or it may be attached to a glove-like article so as to be held on the back of the hand. A short-wave radio communication system serves to transmit signals from the sensor unit 10 to the read-out device 14.

Figure 2:
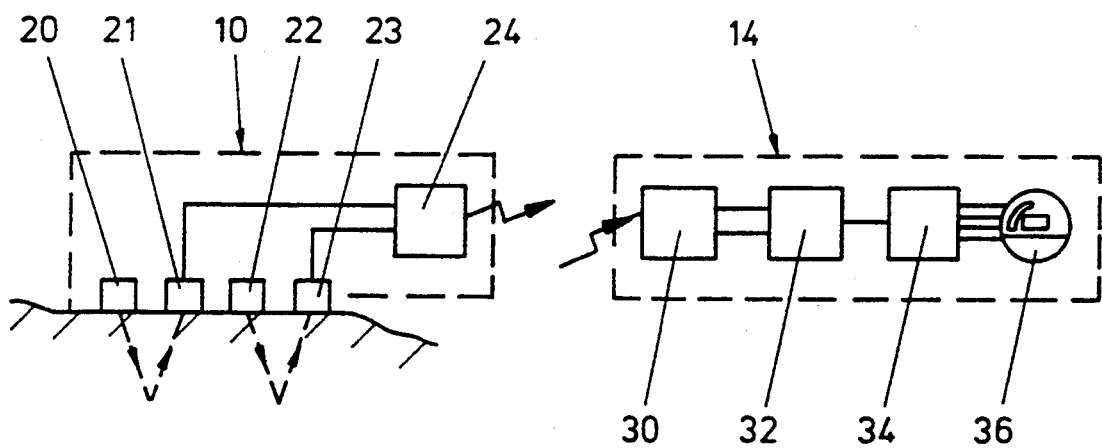
FIG. 2 is a block diagram of the elements of the pulse rate meter.

Referring to FIG. 2, the sensor unit 10 comprises two light emitters 20, 22 and light sensors 21, 23 for receiving light from the respective emitters after reflection within the forehead body tissue. The emitter 20 emits infra red light and the electrical signal provided by the sensor 21 will vary in accordance with the pulsations in the blood flow through the blood vessels in the forehead. The emitter 22 emits light of a different and preferably substantially shorter wavelength, e.g. yellow light, such that the signal from its sensor 23 is relatively independent of variations due to the flow pulsations. Both signals do however vary in accordance with vibrations of the forehead due to movements, and in particular due the feet striking the ground successively as the user jogs. The signals from the two sensors are passed to a short-wave radio transmitter 24 for transmission to the device 14 on the wrist or hand.

The device includes a radio receiver 30 which provides two signals, corresponding to the output signals of the two sensors 21, 23 to a noise cancellation circuit 32. The latter compares one signal with the other, to give a signal varying as the blood flow pulsations but free of the pedometry vibration or noise: the frequency of variations in the resultant signal is determined to give a measure of pulse rate. The signal from noise cancellation circuit 32 is passed to a processor 34 which drives a read-out display device 36. The noise cancellation circuit 32 may be included in the sensor unit 10 worn on the forehead instead of in the device worn on the wrist or hand, in which case the transmitter 24 transmits the noise-free signal. The noise cancellation circuit 32 may carry out a frequency analysis of the output signals from the respective sensors 21, 23: peaks at corresponding frequencies or frequency ranges in the two signals are regarded as noise and the remaining frequency in the signal from the infra red sensor 21 represents the pulse rate. The frequency analysis of each signal may be carried out by fast Fourier Transform (FFT) techniques. Instead, an adaptive noise cancellation technique may be used, in which cross-correlation is performed between the two electrical signals before one is subtracted from the other, so that the noise component can be cancelled even if the pulse and amplitude relations of the two signals vary with time.

Figure 3:
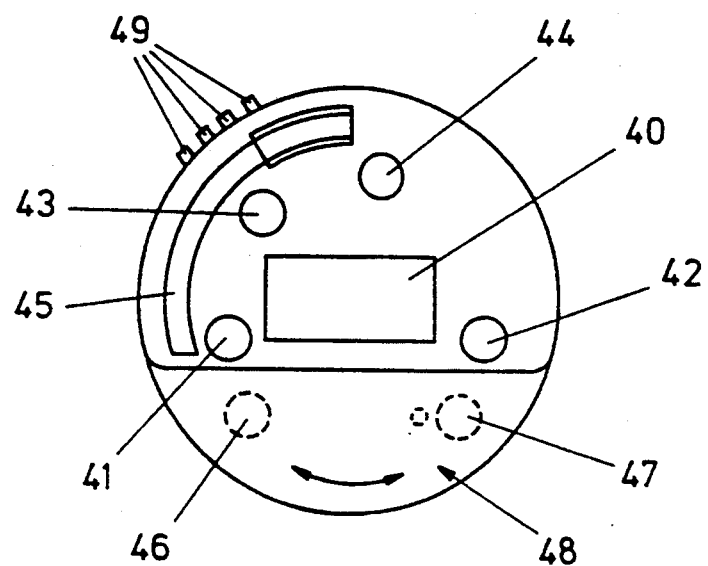
FIG. 3 is a view of the face of the read-out device of the pulse rate meter.

FIG. 3 shows the display device 36 of the device 14 worn on the wrist or hand. The device 36 has a digital display 40 normally giving the time, so that the device may be used as a watch. A digital display 41 adjacent the lower end of a scale 45, gives the at-rest pulse rate and a digital display 42 gives the measured pulse rate. Two digital displays 43, 44 give figures defining the lower and upper limits for pulse rate for the individual when jogging, the so-called training zone. An analogue indication of measured pulse rate is also given over the scale 45, which includes a "window" corresponding to the training zone. The device also has a "male or female" indicator 46 and an "age" display 47 both of which can be covered by turning a mask 48.

In use, the device must be preset for the individual user. The "male or female" selection is made by pressing on of four buttons 49. Successive ages appear on the display 47 by actuation of another one of the buttons until the display shows the age of the user, whereafter the age display remains constant. Then the user puts on the sensor unit 10 and waits for the read-out of measured pulse rate to stabilise. Then another of buttons 49 is pressed, and the pulse rate at that instant (the pulse rate at rest) is thereafter continuously displayed at 41. Alternatively, the device may automatically record and update the at-rest pulse rate each time the actual pulse rate is detected as being lower than that recorded, providing the measured pulse rate is greater than some minimum value (e.g. 40 beats per minute).

From the age, at-rest pulse rate and male or female indication, the processor of the device calculates the training zone, i.e. the lower and upper limits between which the individual concerned should keep his or her pulse rate when training. These limits are displayed in digital terms at 43, 44 and the analogue indicator is correspondingly calibrated.

Then when the wearer is jogging the measured pulse rate is displayed in digital form at 42 and in analogue form at 42 and in analogue form at 45. He or she should aim to maintain the measured pulse rate between the limits of the training zone, i.e. between the values given at 43, 44. This corresponds to keeping the analogue indication within the "window" on the scale 45.

The device keeps a cumulative measure of the time that the measured pulse rate has exceeded the lower limit of the training zone, until this function is reset. The cumulative measure is displayed at 40 instead of the time, by appropriate actuation of the buttons 49. by an alternative actuation of the buttons 49, a stop-watch function is displayed at 40.

Instead of the radio communication link between the sensor unit 10 and the read-out device 14, the read-out device may be connected to the sensor unit by a cable: the read-out device may then be carried in a pocket or clipped onto the user's clothing. Instead, the sensor unit and read-out device may be mounted or combined together and arranged for wearing on the wrist or the back of the hand. In a modification where the sensor unit is worn against the forehead, the read-out display device may also be worn on the head and provide a visible through the wearer's spectacles.

I claim:

1. A pulse responsive device for application to a body, comprising:

a light emitter;

light sensor means for receiving light from said light emitter after transmission through or reflection from body tissue and arranged for providing a first electrical signal having a component varying according to pulsations in blood or other fluid flow through the body tissue;

transducer means arranged for providing a second electrical signal varying according to movements or vibrations of the body to which said transducer means is applied but substantially independent of any blood or other fluid flow pulsations to which said transducer means may be subjected, said transducer means comprising light sensor means responsive to light transmitted through or reflected from the body tissue and of a wavelength such that its absorption or reflectivity is substantially unaffected by pulsations in the blood or other fluid flow; and, means for comparing said first electrical signal and said second electrical signal for providing an output signal varying as the blood or other fluid flow pulsations, but substantially independent of said movements or vibrations of said body.

2. The pulse responsive device according to claim 1, further comprising means for carrying out a frequency analysis of each of said first electrical signal and said second electrical signal and comparing said two frequency analyses for identifying said component which varies according to blood or other fluid flow pulsations for providing said output signal.

3. The pulse responsive device according to claim 1, further comprising means for carrying out adaptive noise cancellation in comparing said first electrical signal and said second electrical signal for providing said output signal.

4. The pulse responsive device according to claim 1, further comprising means for applying said light sensor means and said transducer means, to the forehead of a user.

5. The pulse responsive device according to claim 4, further comprising sensor means which include said light sensor means and said transducer means, said device further comprising a read-out element separate from said sensor means and shortwave radio means for communicating output signals from said sensor means on the forehead of the user to said read-out element.

6. The pulse responsive device according to claim 1, further comprising means for processing said output signal for determining pulse rate.

7. The pulse responsive device according to claim 6, further comprising means for maintaining a cumulative measure of a time period in which the measured pulse rate exceeds a predetermined threshold.

8. The pulse responsive device according to claim 6, further comprising analog indicator means for displaying measured pulse rate, data entry means for entering predetermined data, and means for recalibrating said analog indicator means in accordance with said predetermined data entered via said data entry means.

9. The pulse responsive device according to claim 8, wherein said analog indicator means includes a scale-window corresponding to a training zone, and said recalibration means recalibrates said scale-window in accordance with personal data entered via said data entry means.

10. The pulse responsive device according to claim 1, further comprising means for processing said output signal for determining blood oxygen saturation level.

11. A pulse rate meter, comprising:

transducer means for application to a body and arranged for providing an output signal varying according to pulsations in blood flow through the body;

means for processing said output signal for determining pulse rate;

analog indicator means having a scale for displaying measured pulse rate; and, means for automatically recalibrating said analog indicator means in accordance with a user's resting pulse rate so that a lower end of said scale of said analog indicator means corresponds to said resting pulse rate.

12. The pulse responsive device according to claim 11, wherein said scale includes a window corresponding to a training zone, said pulse rate meter further comprising data entry means for entering predetermined personal data, said means for automatically recalibrating said window in accordance with personal data entered via said data entry means.

13. A pulse responsive device for application to a body, comprising:

a light emitter;

light sensor means for receiving light from said light emitter after transmission through or reflection from body tissue and arranged for providing a first electrical signal having a component varying according to pulsations in blood or other fluid flow through the body tissue;

transducer means arranged for providing a second electrical signal varying according to movements or vibrations of the body to which said transducer means is applied but substantially independent of any blood or other fluid flow pulsations to which said transducer means may be subjected;

means for comparing said first electrical signal and said second electrical signal for providing an output signal varying as the blood or other fluid flow pulsations, but substantially independent of said movements or vibrations of said body; and, means for processing said output signal for determining pulse rate;

analog indicator means for displaying measured pulse rate;

data entry means for entering predetermined data; and, means for recalibrating said analog indicator means in accordance with said predetermined data entered via said data entry means, said analog indicator means including a scale-window corresponding to a training zone, and said recalibration means recalibrates said scale-window in accordance with personal data entered via said data entry means.

* * * * *